United States Patent
Choo et al.

(10) Patent No.: US 12,186,729 B2
(45) Date of Patent: Jan. 7, 2025

(54) SYSTEM AND METHOD FOR MANUFACTURING DIESTER-BASED COMPOSITION

(71) Applicant: LG CHEM, LTD., Seoul (KR)

(72) Inventors: Yeon Uk Choo, Daejeon (KR); Sung Kyu Lee, Daejeon (KR); Joon Ho Shin, Daejeon (KR); Hyoung Jun, Daejeon (KR); Chan Hyu Jin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 617 days.

(21) Appl. No.: 17/600,889

(22) PCT Filed: Jul. 2, 2020

(86) PCT No.: PCT/KR2020/008686
§ 371 (c)(1),
(2) Date: Oct. 1, 2021

(87) PCT Pub. No.: WO2021/002708
PCT Pub. Date: Jan. 7, 2021

(65) Prior Publication Data
US 2022/0177404 A1 Jun. 9, 2022

(30) Foreign Application Priority Data
Jul. 4, 2019 (KR) .................. 10-2019-0080465

(51) Int. Cl.
*B01J 19/00* (2006.01)
*B01D 17/12* (2006.01)
(Continued)

(52) U.S. Cl.
CPC .............. *B01J 19/24* (2013.01); *B01D 17/12* (2013.01); *B01J 19/0046* (2013.01);
(Continued)

(58) Field of Classification Search
CPC ...... B01J 19/24; B01J 19/0046; B01J 19/242; B01J 19/26; B01J 2219/00051;
(Continued)

(56) References Cited

U.S. PATENT DOCUMENTS

| 3,933,630 A | 1/1976 | Helgorsky et al. |
| 2002/0087028 A1 | 7/2002 | Hirata et al. |

(Continued)

FOREIGN PATENT DOCUMENTS

| EP | 2851393 A1 | 3/2015 |
| JP | 2001-261617 A | 9/2001 |

(Continued)

OTHER PUBLICATIONS

Rahman, et al. (2004). The Plasticizer Market: An Assessment of Traditional Plasticizers and Research Trends to Meet New Challenges. Prog. Polym. Sci. vol. 29. pp. 1223-1248.
(Continued)

*Primary Examiner* — Huy Tram Nguyen
(74) *Attorney, Agent, or Firm* — Bryan Cave Leighton Paisner LLP (57) ABSTRACT

The present disclosure relates to a preparation system and a preparation method of a diester-based composition. A first alcohol which is a reaction raw material is added to waste water as an extracting agent, and layer separation is performed to separate a second alcohol which is another reaction raw material in the waste water. Accordingly, the amount of alcohol discharged as waste water can be reduced, and an eco-friendly process operation is possible. In addition, it is economical and efficiency to use the alcohol separated again as a reaction raw material.

16 Claims, 2 Drawing Sheets

(51) Int. Cl.
*B01J 19/24* (2006.01)
*B01J 19/26* (2006.01)
*C02F 1/26* (2023.01)
*C07C 67/03* (2006.01)
*C07C 67/08* (2006.01)
*C07C 67/52* (2006.01)
*C07C 67/58* (2006.01)

(52) U.S. Cl.
CPC ............ *B01J 19/242* (2013.01); *B01J 19/26* (2013.01); *C02F 1/26* (2013.01); *C07C 67/03* (2013.01); *C07C 67/08* (2013.01); *C07C 67/52* (2013.01); *C07C 67/58* (2013.01); *B01J 2219/00051* (2013.01); *B01J 2219/00164* (2013.01)

(58) Field of Classification Search
CPC .... B01J 2219/00164; B01J 2219/00177; B01J 2219/00452; B01J 2219/00495; B01D 17/12; B01D 17/042; C02F 1/26; C07C 67/03; C07C 67/08; C07C 67/52; C07C 67/58; C07C 67/54; C07C 69/80; Y02P 20/582
USPC ........................................................ 422/600
See application file for complete search history.

(56) References Cited

U.S. PATENT DOCUMENTS

| | | |
|---|---|---|
| 2011/0113679 A1 | 5/2011 | Cohen et al. |
| 2012/0197031 A1 | 8/2012 | Firth et al. |
| 2012/0197032 A1 | 8/2012 | Firth et al. |
| 2013/0006012 A1 | 1/2013 | Firth et al. |
| 2013/0035502 A1 | 2/2013 | Cohen et al. |
| 2013/0085288 A1 | 4/2013 | Snead et al. |
| 2013/0165706 A1 | 6/2013 | Firth et al. |
| 2013/0165707 A1 | 6/2013 | Firth et al. |
| 2013/0165708 A1 | 6/2013 | Firth et al. |
| 2013/0204022 A1 | 8/2013 | Snead et al. |
| 2013/0217906 A1 | 8/2013 | Kunz et al. |
| 2014/0121402 A1 | 5/2014 | Snead et al. |
| 2014/0336398 A1 | 11/2014 | Cohen et al. |
| 2014/0336399 A1 | 11/2014 | Cohen et al. |
| 2015/0210855 A1 | 7/2015 | Firth et al. |
| 2015/0240186 A1 | 8/2015 | Cohen et al. |
| 2015/0247107 A1 | 9/2015 | Kunz et al. |
| 2015/0299613 A1 | 10/2015 | Snead et al. |
| 2016/0090343 A1 | 3/2016 | Firth et al. |
| 2016/0362555 A1 | 12/2016 | Firth et al. |
| 2017/0066972 A1 | 3/2017 | Cohen et al. |
| 2018/0044597 A1 | 2/2018 | Cohen et al. |
| 2019/0263745 A1 | 8/2019 | Lee et al. |
| 2021/0040026 A1 | 2/2021 | Lee et al. |

FOREIGN PATENT DOCUMENTS

| | | |
|---|---|---|
| JP | 2010-95467 A | 4/2010 |
| JP | 2010-189335 A | 9/2010 |
| KR | 10-1979-0001531 B1 | 10/1979 |
| KR | 10-1663586 B1 | 10/2016 |
| KR | 10-2018-0074984 A | 7/2018 |
| KR | 10-2018-0129288 A | 12/2018 |
| KR | 10-2019-0027622 A | 3/2019 |
| KR | 10-2019-0027623 A | 3/2019 |

OTHER PUBLICATIONS

Janjua, et al. (2007). Systemic Uptake of Diethyl Phthalate, Dibutyl Phthalate, and Butyl Paraben Following Whole-Body Topical Application and Reproductive and Thyroid Hormone Levels in Humans. Environ. Sci. Technol. vol. 41. pp. 5564-5570.

SYSTEM AND METHOD FOR MANUFACTURING DIESTER-BASED COMPOSITION

CROSS-REFERENCE TO RELATED APPLICATIONS

The present application is a National Phase entry pursuant to 35 U.S.C. § 371 of International Application No. PCT/KR2020/008686, filed on Jul. 2, 2020, and claims the benefit of and priority to Korean Patent Application No. 10-2019-0080465, filed on Jul. 4, 2019, in the Korean Intellectual Property Office, all of which are hereby incorporated by reference in their entirety for all purposes as if fully set forth herein.

TECHNICAL FIELD

The present invention relates to a preparation method and preparation system of a diester-based composition capable of reducing an alcohol concentration in waste water.

BACKGROUND ART

Phthalate-based plasticizers account for 92% of the world plasticizer market until the 20th century (see Mustafizur Rahman and Christopher S. Brazel "The plasticizer market: an assessment of traditional plasticizers and research trends to meet new challenges" Progress in Polymer Science 2004, 29, 1223-1248) and are added as additives for mostly imparting polyvinyl chloride (hereinafter, will referred to as PVC) with flexibility, durability, cold resistance, etc., and reducing the viscosity during melting to improve processability to PVC in various contents and widely used for intimate relation in real life and inevitable direct contact with the human body from hard products such as hard pipes to soft products which may be used in food package materials and blood bags, flooring materials, etc., because of the softness and well-stretching properties thereof when compared to any other materials.

However, despite the compatibility with PVC and excellent softness imparting properties of the phthalate-based plasticizers, recently, in case of using the PVC products containing the phthalate-based plasticizers in real life, controversy over harmfulness has been suggested in that the phthalate-based plasticizers might be released little by little out of the products and act as suspected endocrine disruptors (environmental hormone) and a carcinogen with a heavy metal level (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, after a report has been announced in 1960s in America that the most used di-(2-ethylhexyl) phthalate (DEHP) among phthalate-based plasticizers is released out of PVC products, with added interest on environmental hormone in 1990s, various studies on the harmfulness of phthalate plasticizers to the human body and worldwide environmental regulations have been started.

Accordingly, in order to cope with environmental hormone issues and environmental regulations due to the release of phthalate-based plasticizers, particularly, di(2-ethylhexyl) phthalate, many researchers have proceeded research on developing a novel non-phthalate-based replaceable plasticizers excluding anhydrous phthalic acid which has been used for preparing di(2-ethylhexyl) phthalate, developing phthalate-based plasticizers which may replace di(2-ethylhexyl) phthalate, which may, though phthalate-based, suppress the release of the plasticizer and be used industrially, and developing release-suppressing technique by which the release of phthalate-based plasticizers may be suppressed to markedly reduce the harmfulness to the human body and which may coincide with environmental standards.

As described above, the development of materials which are free from environmental issues and replaceable with di(2-ethylhexyl) phthalate which is a diester-based plasticizer and has the existing environmental issues, is actively being conducted, research on developing diester-based plasticizers having excellent physical properties and research on equipment for preparing such plasticizers are actively being conducted, and the design for more efficient, economic and simple processes in view of process design is required.

Meanwhile, in a process for preparing the diester-based plasticizer above, a batch type process is applied in most industrial sites, and an invention on a gas-liquid separation system for refluxing unreacted materials in a reactor and effective removal of by-products in a batch type process (Korean Laid-open Patent Publication No. 10-2019-0027622), an invention on a system in which equipment for first direct esterification reaction and equipment for second trans esterification are combined for the simplification of equipment for a batch type process (Korean Laid-open Patent Publication No. 10-2019-0027623), etc. have been disclosed. However, such inventions employ a batch type process, and there are limitations on the improvement of refluxing amount or steam amount, productivity is very low, and there are limitations on technique applicable for improvement.

In addition, as a continuous process, an invention relating to a process composing a reaction part through connecting two or more reactors in series (Korean Registration Patent Publication No. 10-1663586) has been disclosed, but is an invention relating to the control of the reaction temperature for accomplishing a target modification ratio, and there are limitations on improving a process and saving energy.

PRIOR ART DOCUMENTS

Patent Documents (Patent Document 1) Korean Laid-open Patent Publication No. 10-2019-0027622
(Patent Document 2) Korean Laid-open Patent Publication No. 10-2019-0027623
(Patent Document 3) Korean Registration Patent Publication No. 10-1663586

Non-Patent Documents (Non-patent document 1) Mustafizur Rahman and Christopher S. Brazel "The plasticizer market: an assessment of traditional plasticizers and research trends to meet new challenges" Progress in Polymer Science 2004, 29, 1223-1248
(Non-patent document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

The purpose of the present invention is to provide an eco-friendly preparation method and a preparation system for a diester-based composition, by which a diester-based composition can be efficiently and economically prepared through efficient recovery of an alcohol in waste water discharged from a process, and the concentration of an alcohol in waste water is low.

Technical Solution

The present invention provides a preparation system of a diester-based composition, including a first purification part including a purification space for separating a reaction product of esterification reaction of a dicarboxylic acid and a first alcohol into a purified product and the first alcohol which is an unreacted reactant, and a purified product line and an unreacted reactant recovering line for discharging the purified product and the unreacted reactant, a trans reaction unit including an interior space for performing trans esterification reaction of the purified product injected from the purified product line of the first purification part and a second alcohol injected from a separate alcohol injection part, and a trans reaction product line discharging a produced trans reaction product, a neutralized water separating apparatus including a partition wall separating an interior part into a neutralization space and a water separation space and forming a passage capable of moving a fluid, and an organic layer line and a waste water line for separately discharging an ester-rich organic layer and a water-rich waste water layer from the water separation space, the trans reaction product line being connected with the neutralization space, a second purification part including an unreacted reactant recovering line, a second waste water line and a product line for separately discharging the ester-rich organic layer injected from the organic layer line of the neutralized water separating apparatus into three streams of a mixed alcohol of the unreacted first alcohol and the second alcohol, a mixed waste water including water, the first alcohol and the second alcohol, and a diester-based composition, and a waste water treating unit including a waste water injecting line which is connected with the waste water line of the neutralized water separating apparatus and the second waste water line of the second purification part, an extracting agent injecting line injecting the first alcohol which is an extracting agent, a layer separating space for layer separating a mixed waste liquid of water, the first alcohol and the second alcohol into a mixed alcohol layer and a waste water layer, and a mixed alcohol recovering line and a final waste water line, separately discharging the mixed alcohol layer and the waste water layer.

In addition, the present invention provides a preparation method of a diester-based composition performed through the preparation system.

Advantageous Effects

In the preparation system and the preparation method of the present invention, an alcohol discharged as waste water can be recovered, and an eco-friendly operation is possible, and the economic feasibility and efficiency of an overall process can be improved through reusing the recovered alcohol as a reaction raw material.

BEST MODE FOR CARRYING OUT THE INVENTION

Hereinafter, preferred embodiments will be suggested to assist the understanding of the present invention. However, the embodiments are only for illustrating the present invention but are not intended to limit the scope of the present invention.

Examples and Comparative Example

Figure 1:
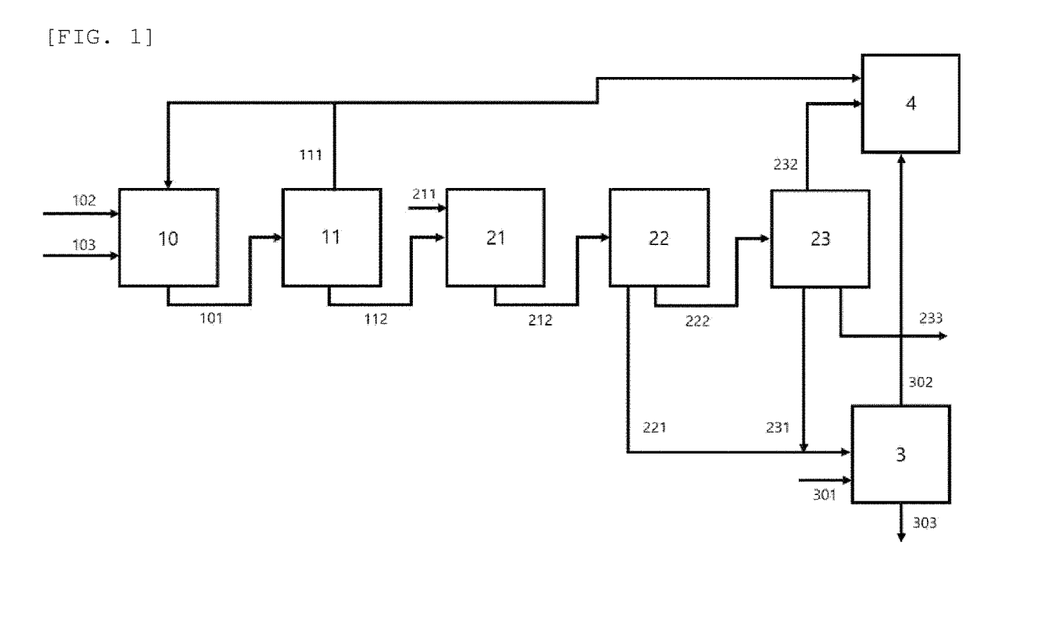
FIG. 1 and FIG. 2 are simplified diagrams of the preparation systems of a diester-based composition according to embodiments of the present invention.

After constituting the preparation system as in FIG. 1, terephthalic acid was used as a dicarboxylic acid, 2-ethylhexyl alcohol was used as a first alcohol, and n-butanol was used as a second alcohol, and by changing the temperature of a layer separator and the injection ratio of the first alcohol, the recovery ratio of the first alcohol and the second alcohol, the alcohol concentration in waste water discharged, BOD and COD values, and water content and water amount of an alcohol layer injected from a waste water treating unit to a mixed alcohol tank were measure. The results are shown in Table 1 below.

TABLE 1

|  | Layer separator temperature (° C.) | First alcohol injection ratio (%) | First alcohol recovery ratio (%) | Second alcohol recovery ratio (%) | Alcohol concentration in waste water (%) | BOD in waste water (ppm) | COD in waste water (ppm) | Alcohol layer water content (%) | Alcohol layer water amount (kg/hr) |
|---|---|---|---|---|---|---|---|---|---|
| Comparative Example | 74 |  | 0 | 0 | 2.08 | 37,109 | 61,849 | — | — |
| Example 1-1 | 70 | 10 | 99.03 | 52.35 | 1.10 | 19,489 | 32,482 | 9.83 | 28.8 |
| Example 1-2 | 75 | 10 | 98.95 | 53.72 | 1.08 | 19,175 | 31,958 | 9.97 | 29.3 |
| Example 2-1 | 60 | 30 | 99.72 | 74.70 | 0.64 | 11,217 | 18,694 | 9.50 | 79 |
| Example 2-2 | 70 | 30 | 99.66 | 76.93 | 0.61 | 10,767 | 17,945 | 9.73 | 81 |
| Example 2-3 | 80 | 30 | 99.60 | 78.62 | 0.59 | 10,544 | 17,573 | 9.98 | 83 |

TABLE 1-continued

|  | Layer separator temperature (° C.) | First alcohol injection ratio (%) | First alcohol recovery ratio (%) | Second alcohol recovery ratio (%) | Alcohol concentration in waste water (%) | BOD in waste water (ppm) | COD in waste water (ppm) | Alcohol layer water content (%) | Alcohol layer water amount (kg/hr) |
|---|---|---|---|---|---|---|---|---|---|
| Example 3-1 | 60 | 50 | 99.83 | 83.44 | 0.46 | 8,095 | 13,491 | 9.48 | 129 |
| Example 3-2 | 70 | 50 | 99.80 | 85.01 | 0.44 | 7,872 | 13,119 | 9.70 | 132 |
| Example 3-3 | 80 | 50 | 99.76 | 86.17 | 0.44 | 7,833 | 13,055 | 9.93 | 136 |
| Example 3-4 | 90 | 50 | 99.72 | 87.00 | 0.44 | 7,957 | 13,262 | 10.18 | 139 |

As confirmed from the table above, if the preparation method and the preparation system of the present invention are used, the first alcohol and the second alcohol, which are reaction raw materials can be recovered in high recovery ratio and reused as the reaction raw materials, and it was confirmed that the alcohol content in waste water was small, and BOD and COD values were also low, it is eco-friendly. Particularly, when compared with the Comparative Example in which a layer separator was not installed, the reduction effects of an alcohol concentration in waste water by at least about 50% were confirmed, and BOD and COD values also were reduced to at least half. Meanwhile, it was confirmed that if an extracting agent was injected in a large amount, the recovery ratio of an alcohol increased, and the alcohol concentration in waste water tended to decrease as well, but the water amount of an alcohol layer was increased, which has a trade-off relation. It was also confirmed that with the increase of the temperature of the layer separator, the alcohol concentration in waste water was increased.

MODE FOR CARRYING OUT THE INVENTION

Hereinafter, the present invention will be explained in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Preparation System of Diester-Based Composition

The present invention provides a preparation system of a diester-based composition, including a first purification part including a purification space for separating a reaction product of esterification reaction of a dicarboxylic acid and a first alcohol into a purified product and the first alcohol which is an unreacted reactant, and a purified product line and an unreacted reactant recovering line for discharging the purified product and the unreacted reactant, a trans reaction unit including an interior space for performing trans esterification reaction of the purified product injected from the purified product line of the first purification part and a second alcohol injected from a separate alcohol injection part, and a trans reaction product line discharging a produced trans reaction product, a neutralized water separating apparatus including a partition wall separating an interior part into a neutralization space and a water separation space and forming a passage capable of moving a fluid, and an organic layer line and a waste water line for separately discharging an ester-rich organic layer and a water-rich waste water layer from the water separation space, the trans reaction product line being connected with the neutralization space, a second purification part including an unreacted reactant recovering line, a second waste water line and a product line for separately discharging the ester-rich organic layer injected from the organic layer line of the neutralized water separating apparatus into three streams of a mixed alcohol of the unreacted first alcohol and the second alcohol, a mixed waste water including water, the first alcohol and the second alcohol, and a diester-based composition, and a waste water treating unit including a waste water injecting line which is connected with the waste water line of the neutralized water separating apparatus and the second waste water line of the second purification part, an extracting agent injecting line injecting the first alcohol which is an extracting agent, a layer separating space for layer separating a mixed waste liquid of water, the first alcohol and the second alcohol into a mixed alcohol layer and a waste water layer, and a mixed alcohol recovering line and a final waste water line, separately discharging the mixed alcohol layer and the waste water layer.

Hereinafter, the preparation system of the present invention will be explained referring to attached drawings.

The preparation system of the present invention mainly includes five parts of a first purification part (11), a trans reaction unit (21), a neutralized water separating apparatus (22), a second purification part and a waste water treating unit (3) according to function, and can further include an ester reaction unit (10), a mixed alcohol tank (4) and an alcohol recovering part (5).

As shown in FIG. 1, a dicarboxylic acid stream (102) and a first alcohol stream (103) are injected into an ester reaction unit, and through esterification reaction in the ester reaction unit, a reaction product is prepared. In case of performing esterification reaction between a dicarboxylic acid and an alcohol, the temperature required for the reaction can frequently be similar to or higher than the boiling point of the alcohol which is a reaction raw material, and due to the vaporization of the alcohol which is a reaction raw material during performing the reaction, an insufficient degree of a conversion ratio is frequently obtained. Accordingly, a greater amount of alcohol than an amount required for practical reaction is injected for performing esterification reaction, and as a result, in the reaction product, an unreacted first alcohol remaining without participating in the reaction and water which is a by-product of the esterification reaction can remain as well as a diester-based compound which is the resultant material of the reaction. Accordingly, the unreacted first alcohol and water included in the reaction product are required to be removed, and this process is performed in a next first purification part (11). Meanwhile, in this regard, the alcohol vaporized during the reaction is required to be injected again into the reaction unit, and accordingly, the ester reaction unit of the present invention can be provided with a refluxing apparatus.

A reaction product stream (101) produced through the esterification reaction is injected into the first purification part (11), and an unreacted first alcohol in the reaction product is removed in a purification space in the first purification part. The removal of the unreacted first alcohol can be performed by various methods, and can be performed through a method such as distillation considering that the boiling point of the diester-based compound is higher than the boiling point of the first alcohol. In this case, the first purification part can have a shape such as a column. An unreacted first alcohol stream (111) removed in this process can be discharged from the first purification part through an unreacted reactant recovering line and then, injected again into any one or both of the ester reaction unit and a mixed alcohol tank (4), and a purified product stream (112) is transported through a purified product line to a trans reaction unit (21).

Trans esterification reaction is performed between the diester-based compound in the purified product injected from the first purification part to the trans reaction unit and a second alcohol (211) injected into the trans reaction unit (21). As a result, a diester-based compound substituted with an alkyl group and the first alcohol is produced again, and a trans reaction product including the diester-based compound, the first alcohol produced, and an unreacted second alcohol is transported to a next purified water separating apparatus (22). In addition, like in the ester reaction unit, if considering that the boiling point of the second alcohol is lower than the boiling point of the first alcohol, the vaporization of the second alcohol can arise in the trans reaction unit, and accordingly, the trans reaction unit can also be provided with a refluxing apparatus for injecting the vaporized alcohol into the trans reaction unit again.

The trans reaction product transported to the neutralized water separating apparatus becomes a target for neutralization. Considering that since the esterification reaction is performed in acidic conditions, an acidic material, for example, an acidic catalyst can remain in the trans reaction product, and the dicarboxylic acid corresponding to the reaction raw material also is an acidic material, the neutralization of the trans reaction product is necessary. The interior space of the neutralized water separating apparatus is divided into a neutralization space and a water separation space, and the trans reaction product neutralized in the neutralization space moves through a passage to the water separation space and layer is separated into an organic layer and a waste water layer. Water is produced through neutralization reaction, and since the first alcohol not removed in advance has better affinity with water than the diester-based compound, an ester, i.e., the diester-based compound is rich in the separated organic layer, and a plentiful amount of water and a trace amount of the first alcohol are included in the waste water layer. A separated organic layer stream (222) is transported through an organic layer line to a second purification part (23), and a waste water layer stream (221) is transported to a waste water treating unit (3). The waste water stream transported to the waste water treating unit includes water and the second alcohol, and the concentration of the second alcohol in the stream can be 0.01 to 10 wt %, 0.1 to 7 wt %, or 1 to 5 wt %.

The water, first alcohol and second alcohol in the organic layer separated in the neutralized water separating apparatus are removed in the next second purification part. As previously performed in the first purification part and the neutralized water separating apparatus, a mixed alcohol (232) of the unreacted first alcohol and the second alcohol separated in this second purification part, and a second waste water (231) including water and remaining alcohol are respectively discharged, and the second waste water is transported to a waste water treating unit (3). A diester-based composition (233) corresponding to a final product is also separately discharged. The second waste water transported to the waste water treating unit includes water, the first alcohol and the second alcohol, and the concentration of the second alcohol in the second waste water can be 0.01 to 10 wt % or 0.1 to 5 wt % based on the total weight of the second waste water.

As described above, the waste water and the second waste water produced during the operation process of the neutralized water separating apparatus and the second purification part include water together with the first alcohol and the second alcohol, and the separation of the first alcohol and the second alcohol in the waste water and the reuse thereof are technical characteristics of the present invention. To accomplish the characteristics, the preparation system of the present invention includes a waste water treating unit (3). The waste water (221) and the second waste water (231) transported to the waste water treating unit include a large amount of water together with the first alcohol and the second alcohol, and particularly, the second alcohol having a small carbon atom number generally has good affinity with water, and the alcohols are present in a well miscible state with water. Accordingly, to separate the alcohol in the waste water, it is not necessary to separately inject an extracting agent which has excellent affinity with the second alcohol and relatively deteriorated affinity with water, but in the present invention, the first alcohol stream 301 corresponding to a reaction raw material is injected into the waste water treating unit as the extracting agent.

Generally, as the extracting agent for separating layers, various materials can be utilized according to the components of a mixture which is a target for separating layers, but in order to select an extracting agent applicable to a series of the preparation system as in the present invention, various conditions are considered. For example, the extracting agent is also applied as impurities in a point of view, and the extracting agent remained can be required to be removed through an additional process afterward, and a separate apparatus for storing and injecting the extracting agent is also required. Accordingly, by using the first alcohol corresponding to a reaction raw material as the extracting agent, a portion of the reaction raw material can be used only with a line for additional injection without a separate storing apparatus. The resultant separated layer by using the extracting agent becomes a mixed alcohol layer of the first alcohol and the second alcohol and includes the same components as the mixed alcohol layer obtained through the removal of the unreacted alcohol in advance, and thus, the separated layer can be directly injected into the mixed alcohol tank without separate treatment, thereby improving the efficiency of a whole process. In addition, since the first alcohol used as the extracting agent is not removed but remain as a mixed alcohol type in the process, the first alcohol can be used as a fuel for generating steam for heating a reactor, etc. afterward, or the first alcohol can be separated and used as the reaction raw material or the extracting agent again, thereby markedly improving the economic feasibility of the process as well.

By controlling the temperature of the layer separation space in the waste water treating unit, more efficient layer separation can be achieved, and the waste water treating unit can further include a temperature controlling part for controlling the temperature of the layer separation space. The temperature controlling part can be any means that can control the temperature of the layer separation space, without specific limitation, and for example, a means such as a flowing amount controlling valve of a steam injecting line, capable of controlling the amount of steam used for heating the waste water treating unit, and a heating furnace or a heating jacket, capable of directly heating a layer separator, can be used as the temperature controlling part.

Like the temperature controlling, more efficiency layer separation can be achieved by controlling the amount of the first alcohol injected as the extracting agent into the waste water treating unit, and for this purpose, the waste water treating unit can include a flowing amount controlling part controlling a flowing amount. The flowing amount controlling part can be any one capable of controlling the flowing amount of the first alcohol without specific limitation, and for example, a means such as a flowing amount controlling valve applied to a first alcohol injecting line can be used.

By the first alcohol injected, the mixed waste water of water, the first alcohol and the second alcohol is separated into a mixed alcohol layer rich in the first alcohol and the second alcohol and a waste water layer rich in water, and a separated mixed alcohol stream (302) and a final waste water stream (303) are separated and discharged, individually. The alcohol content in the final waste water stream discharged is markedly reduced through the previous treatment, and the mixed alcohol stream can be immediately used as a fuel or stored in the mixed alcohol tank (4), etc. which can be additionally included in the system of the present invention and utilized afterward.

The shape of the waste water treating unit is not specifically limited, for example, a bath shape like a waste water treating bath, or a decanter or extracting column shape, etc., and the waste water treating unit can be a single apparatus capable of performing the above-described function, or a unit composed by connecting multiple apparatuses.

The preparation system of the present invention can include a mixed alcohol tank (4). The mixed alcohol tank plays the role of mixing and storing the mixed alcohol of the first alcohol and the second alcohol, removed in the second purification part in advance and the mixed alcohol separated from the waste water treating unit, and in case where the unreacted first alcohol stream removed in the first purification part is transported to the mixed alcohol tank, the unreacted first alcohol can also be mixed and stored together. If the unreacted alcohol and the mixed alcohol recovered from the waste water are stored in this way, treatment including removing remaining impurities through a purification process, etc. is easy afterward, and there are advantages in applying in a different way during operation according to needs.

Figure 2:
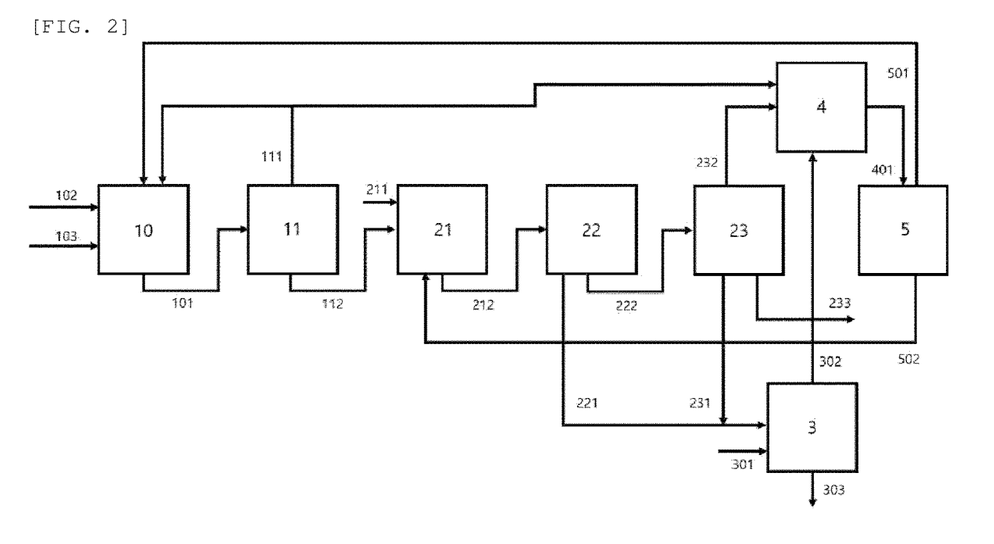

In addition, as shown in FIG. 2, the preparation system of the present invention can further include an alcohol recovering part (5). In case where the preparation system of the present invention includes the aforementioned mixed alcohol tank, in order to separate alcohols present in a mixed type and use as a reaction raw material or an extracting agent, the separation thereof is necessary, and in this case, the first alcohol and the second alcohol can be separated through the alcohol recovering part. A first alcohol stream (501) separated in the interior purification space of the alcohol recovering part is transported to an ester reaction unit (10), and a second alcohol stream (502) is transported to a trans reaction unit (21) to be used as reaction raw materials, and a portion of the first alcohol stream can be transported to the waste water treating unit again and utilized as an extracting agent.

The preparation system of a diester-based composition of the present invention is continuously operated. Since the preparation system of the present invention is continuously operated, each stream can be kept constant, and the volume of the waste water treating unit can be kept small, and accordingly, the overall process is even further economical.

Preparation Method of Diester-Based Composition

The present invention provides a preparation method of a diester-based composition, including a step of removing an unreacted first alcohol in a reaction product produced by esterification reaction of a dicarboxylic acid and a first alcohol to obtain a purified product (S1), a step of performing trans esterification reaction of the purified product and a second alcohol to obtain a trans reaction product (S2), a step of separating a water-rich waste water layer and an ester-rich organic layer by neutralizing the trans reaction product and separating water, and transporting the waste water layer to a waste water treating unit (S3), a step of separating the ester-rich organic layer into three streams of a diester-based composition, a mixed alcohol of an unreacted first alcohol and the second alcohol, and a second waste water including water, the first alcohol and the second alcohol, and transporting the second waste water to the waste water treating unit (S4), and a step of injecting an extracting agent to the waste water treating unit for layer separating the mixed waste water into a final waste water layer and a mixed alcohol layer (S5), wherein the extracting agent includes the first alcohol.

The preparation method of a diester-based composition can be performed through the above-explained preparation system of a diester-based composition, and step S1 is performed in the ester reaction unit and the first purification part, step S2 is performed in the trans reaction unit, step S3 is performed in the purified water separating apparatus, step S4 is performed in the second purification part, and step S5 is performed in the waste water treating unit.

In addition, in the preparation method, the unreacted mixed alcohol stream separated in step S4 and the mixed alcohol layer separated in step S5 are transported to the mixed alcohol tank, and a step of separating the mixed alcohol of the mixed alcohol tank into the first alcohol and the second alcohol (S6) can be further included. Step S6 can be performed in the above-explained alcohol recovering part. The first alcohol separated in step S6 is used for the esterification reaction in step S1, and the second alcohol separated can be used for the trans esterification reaction in step S3. Meanwhile, in addition to the unreacted mixed alcohol stream and the mixed alcohol layer, in case of transporting the unreacted first alcohol stream removed in the first purification part to the mixed alcohol tank, the mixed alcohol of the mixed alcohol tank can also be separated into the first alcohol and the second alcohol and used.

In the preparation method of the present invention, the temperature of the waste water treating unit in step S5 can be 50 to 100° C., preferably, 60 to 90° C. If the temperature of the waste water treating unit is lower than the range, energy required for the layer separation may be insufficiently supplied, and the layer separation may not be performed unfavorably, and if the temperature is higher than the range, alcohol or water included in the waste water treating unit may be vaporized and act as the inhibiting factor of the layer separation.

In the preparation method of the present invention, the injection ratio (wt %) of the first alcohol injected into the waste water treating unit in step S5 with respect to the total amount of waste water injected can be 5 to 60%, preferably, 10 to 50%. If the extracting agent is injected in an amount greater than the range, there are problems in that the alcohol separating efficiency in the waste water may not be improved in view of the amount used of the extracting agent, and at the same time, the water content in the mixed alcohol layer recovered may rather increase, and if the amount injected is less than the range, the layer separation itself may not be easily achieved.

In the preparation system and preparation method of the present invention, the dicarboxylic acid can be selected from the group consisting of phthalic acid, terephthalic acid, isophthalic acid and cyclohexane dicarboxylic acid, the first alcohol can be a primary alcohol having a carbon number of 7 to 12, and the second alcohol can be a primary alcohol having a carbon number of 3 to 6. The primary alcohol can include both linear or branch type primary alcohols. The diester-based composition prepared using such a dicarboxylic acid and an alcohol has advantages of excellent performance as a plasticizer.

EXPLANATION OF SYMBOLS

10: ester reaction unit
101: esterification reaction product stream of dicarboxylic acid and first alcohol
102: dicarboxylic acid stream
103: first alcohol stream
11: first purification part
111: removed unreacted first alcohol stream
112: purified product stream
21: trans reaction unit
211: second alcohol stream
212: trans reaction product stream
22: neutralized water separating apparatus
221: waste water stream
222: organic layer stream
23: second purification part
231: second waste water stream
232: removed mixed alcohol stream
233: product stream
3: waste water treating unit
301: first alcohol stream
302: mixed alcohol stream
303: final waste water stream
4: mixed alcohol tank
401: mixed alcohol stream
5: alcohol recovering part
501: first alcohol recovering stream
502: second alcohol recovering stream

The invention claimed is:

1. A preparation system of a diester-based composition, the system comprising:
a first purification part comprising a purification space for separating a reaction product of esterification reaction of a dicarboxylic acid and a first alcohol into a purified product and the first alcohol which is an unreacted reactant, and a purified product line and an unreacted reactant recovering line for discharging the purified product and the unreacted reactant;
a trans reaction unit comprising an interior space for performing trans esterification reaction of the purified product injected from the purified product line of the first purification part and a second alcohol injected from a separate alcohol injection part, and a trans reaction product line discharging a produced trans reaction product;
a neutralized water separating apparatus comprising a partition wall separating an interior part into a neutralization space and a water separation space and forming a passage capable of moving a fluid, and an organic layer line and a waste water line for separately discharging an ester-rich organic layer and a water-rich waste water layer from the water separation space, the trans reaction product line being connected with the neutralization space;
a second purification part comprising an unreacted reactant recovering line, a second waste water line and a product line for separately discharging the ester-rich organic layer injected from the organic layer line of the neutralized water separating apparatus into three streams of a mixed alcohol of the unreacted first alcohol and the second alcohol, a mixed waste water comprising water, the first alcohol and the second alcohol, and a diester-based composition; and
a waste water treating unit comprising a waste water injecting line which is connected with the waste water line of the neutralized water separating apparatus and the second waste water line of the second purification part, an extracting agent injecting line injecting the first alcohol which is an extracting agent, a layer separating space for layer separating a mixed waste liquid of water, the first alcohol and the second alcohol into a mixed alcohol layer and a waste water layer, and a mixed alcohol recovering line and a final waste water line, separately discharging the mixed alcohol layer and the waste water layer.

2. The preparation system of a diester-based composition according to claim 1, wherein the unreacted reactant recovering line of the second purification part and the mixed alcohol recovering line of the waste water treating unit further comprise a mixed alcohol tank connected with an interior mixed alcohol storing space.

3. The preparation system of a diester-based composition according to claim 2, wherein the preparation system further comprises an ester reaction unit performing esterification reaction of the dicarboxylic acid and the first alcohol, and wherein the unreacted reactant recovering line of the first purification part is connected with one or more of the ester reaction unit and the mixed alcohol tank.

4. The preparation system of a diester-based composition according to claim 2, wherein the mixed alcohol tank comprises a mixed alcohol discharging line discharging the mixed alcohol stored, and
wherein the preparation system further comprises an alcohol recovering part comprising a mixed alcohol injecting line connected with the mixed alcohol discharging line, a purification space separating the mixed alcohol into the first alcohol and the second alcohol, and a first alcohol recovering line and a second alcohol recovering line respectively discharging the first alcohol and the second alcohol separated.

5. The preparation system of a diester-based composition according to claim 1, wherein the waste water treating unit further comprises a temperature controlling part controlling a temperature of the layer separating space.

6. The preparation system of a diester-based composition according to claim 1, wherein the waste water treating unit further comprises a flowing amount controlling part controlling a flowing amount of the first alcohol injected as the extracting agent.

7. The preparation system of a diester-based composition according to claim 1, wherein a stream in the waste water line of the neutralized water separating apparatus comprises water and the second alcohol, and a concentration of the second alcohol in the stream is 0.01 to 10 wt %.

8. The preparation system of a diester-based composition according to claim 1, wherein a stream in the second waste water line of the second purification part comprises water, the first alcohol and the second alcohol, and a concentration of the second alcohol in the stream is 0.01 to 10 wt %.

9. The preparation system of a diester-based composition according to claim 1, wherein the preparation system is operated by a continuous type.

10. A preparation method of a diester-based composition, the method comprising:
  a step of removing an unreacted first alcohol from a reaction product produced by esterification reaction of a dicarboxylic acid and a first alcohol to obtain a purified product (S1);
  a step of performing trans esterification reaction of the purified product and a second alcohol to obtain a trans reaction product (S2);
  a step of separating a water-rich waste water layer and an ester-rich organic layer by neutralizing the trans reaction product and separating water, and transporting the waste water layer to a waste water treating unit (S3);
  a step of separating the ester-rich organic layer into three streams of a diester-based composition, a mixed alcohol of an unreacted first alcohol and the second alcohol, and a second waste water comprising water, the first alcohol and the second alcohol, and transporting the second waste water to the waste water treating unit (S4); and
  a step of injecting an extracting agent to the waste water treating unit for layer separating the mixed waste water into a final waste water layer and a mixed alcohol layer (S5),
  wherein the extracting agent comprises the first alcohol.

11. The preparation method of a diester-based composition according to claim 10, wherein the mixed alcohol stream separated in step S4 and the mixed alcohol layer separated in step S5 are transported to a mixed alcohol tank, and
  wherein the method further comprises a step of separating the mixed alcohol in the mixed alcohol tank into the first alcohol and the second alcohol (S6).

12. The preparation method of a diester-based composition according to claim 11, wherein the first alcohol separated in step S6 is used for the esterification reaction in step S1, and the separated second alcohol is used for the trans esterification reaction in step S2.

13. The preparation method of a diester-based composition according to claim 10, wherein a temperature of the waste water treating unit in step S5 is 50 to 100° C.

14. The preparation method of a diester-based composition according to claim 10, wherein an injection ratio of the first alcohol injected into the waste water treating unit as the extracting agent in step S5 is 5 to 60%.

15. The preparation method of a diester-based composition according to claim 10, wherein the dicarboxylic acid is selected from the group consisting of phthalic acid, terephthalic acid, isophthalic acid and cyclohexane dicarboxylic acid.

16. The preparation method of a diester-based composition according to claim 10, wherein the first alcohol is an alcohol having a carbon number of 7 to 12, and the second alcohol is an alcohol having a carbon number of 3 to 6.

* * * * *